United States Patent
Aberton et al.

(10) Patent No.: US 12,201,545 B2
(45) Date of Patent: Jan. 21, 2025

(54) KNEE THERAPY DEVICE

(71) Applicants: Mark Aberton, Holladay, UT (US);
Kyle Aberton, Holldaday, UT (US)

(72) Inventors: Mark Aberton, Holladay, UT (US);
Kyle Aberton, Holldaday, UT (US)

( * ) Notice: Subject to any disclaimer, the term of this patent is extended or adjusted under 35 U.S.C. 154(b) by 226 days.

(21) Appl. No.: 17/884,444

(22) Filed: Aug. 9, 2022

(65) Prior Publication Data

US 2024/0050259 A1 Feb. 15, 2024

(51) Int. Cl.
| A61F 5/01 | (2006.01) |
| A61H 1/02 | (2006.01) |
| A63B 21/00 | (2006.01) |
| A63B 21/002 | (2006.01) |
| A63B 21/055 | (2006.01) |
| A63B 23/035 | (2006.01) |

(52) U.S. Cl.
CPC .......... *A61F 5/0125* (2013.01); *A61H 1/024* (2013.01); *A63B 21/00069* (2013.01); *A63B 21/00185* (2013.01); *A63B 21/0023* (2013.01); *A63B 21/055* (2013.01); *A63B 23/035* (2013.01); *A61H 2201/0134* (2013.01); *A61H 2201/1642* (2013.01); *A61H 2203/0431* (2013.01)

(58) Field of Classification Search
CPC ............. A61F 5/0125; A63B 21/00069; A63B 21/00185; A63B 21/0023; A63B 21/055; A61H 2201/0134; A61H 2201/1642; A61H 2203/0431
See application file for complete search history.

(56) References Cited

U.S. PATENT DOCUMENTS

| 4,185,818 | A | * | 1/1980 | Brentham | .......... A63B 23/0488 482/112 |
| 4,844,454 | A | * | 7/1989 | Rogers | .................... A61H 1/024 482/131 |
| 5,236,333 | A | * | 8/1993 | Barba, Jr. | .............. A61H 1/024 602/5 |
| 11,083,662 | B2 | * | 8/2021 | Marti | ............... A63B 21/00185 |
| 11,701,288 | B2 | * | 7/2023 | Marti | .................... A63B 21/055 601/34 |
| 2002/0193210 | A1 | * | 12/2002 | Turner | ............... A63B 21/4047 482/80 |
| 2008/0207413 | A1 | * | 8/2008 | Gonzalez | ............. A61H 1/0218 482/144 |
| 2011/0224585 | A1 | * | 9/2011 | Hall | ....................... A61H 1/008 601/34 |
| 2018/0104130 | A1 | * | 4/2018 | Sampson | ............... A61H 1/024 |

* cited by examiner

*Primary Examiner* — Megan Anderson
*Assistant Examiner* — Andrew M Kobylarz
(74) *Attorney, Agent, or Firm* — Superior IP, PLLC; Dustin L. Call

(57) ABSTRACT

A knee therapy device. The knee therapy device includes one or more legs, the one or more legs configured to support the knee therapy device and a frame, the frame attached to the one or more legs. The knee therapy device also includes a thigh pad attached to the frame, where the thigh pad is configured to support the thigh of a user. The knee therapy device further includes a lower leg support, where the lower leg support is attached to the frame, is configured to support the lower leg of the user and moves relative to the frame about a hinge point.

14 Claims, 5 Drawing Sheets

KNEE THERAPY DEVICE

CROSS-REFERENCE TO RELATED APPLICATIONS

Not applicable.

BACKGROUND OF THE INVENTION

Knee therapy devices allow a user to move his/her knee as part of rehabilitating the knee joint. This can be done, for example, after surgery or injury which prevents normal use of the user's knee joint. I.e., these devices are designed to help the user move his/her knee in order to strengthen, mobilize and manipulate the user's knees.

Nevertheless, knee therapy devices include a number of drawbacks. For example, these devices tend to be bulky and complicated. That means that the device is placed and then the user must come to the device. This means, in turn, that the user only spends a limited amount of time with the therapy device. However, in many instances if the user can use passive motion (i.e., move his/her knee without using leg muscles) then it is improbable for the user to overdo therapy. That is, a user can overdo strength training on the joint but not passive flexing of the joint.

In addition, these devices are only passive (something moves the joint besides the user's leg muscles) or only active (only the user's muscles move the leg joint). However, a combination of passive and active movement makes more sense in rehabilitation of a user's knee joint, this is known as active-assisted range of motion.

Accordingly, there is a need in the art for a knee therapy device which is portable. Further, there is a need in the art for the device to allow a full spectrum of movement of the joint, both active, passive and active-assisted movement of the joint.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a knee therapy device. The knee therapy device includes one or more legs, the one or more legs configured to support the knee therapy device and a frame, the frame attached to the one or more legs. The knee therapy device also includes a thigh pad attached to the frame, where the thigh pad is configured to support the thigh of a user. The knee therapy device further includes a lower leg support, where the lower leg support is attached to the frame, is configured to support the lower leg of the user and moves relative to the frame about a hinge point.

Another example embodiment includes a knee therapy device. The knee therapy device includes a base, the base configured to support the knee therapy device and one or more legs attached to the base. The knee therapy device also includes a frame, the frame attached to the one or more legs and a thigh pad attached to the frame, where the thigh pad is configured to support the thigh of a user. The knee therapy device further includes a lower leg support, where the lower leg support is attached to the frame and is configured to support the lower leg of the user. The knee therapy device additionally includes a hinge, where the hinge allows the lower leg support to move relative to the frame and a strap, where the strap is configured to secure the user's lower leg relative to the lower leg support.

Another example embodiment includes a knee therapy device. The knee therapy device includes a base, the base configured to support the knee therapy device and one or more legs attached to the base. The knee therapy device also includes a frame, the frame attached to the one or more legs and a thigh pad attached to the frame, where the thigh pad is configured to support the thigh of a user. The knee therapy device further includes a lower leg support, where the lower leg support is attached to the frame and is configured to support the lower leg of the user. The knee therapy device additionally includes a hinge, where the hinge allows the lower leg support to move relative to the frame and a strap, where the strap is configured to secure the user's lower leg relative to the lower leg support. The knee therapy device moreover includes a handle, where the handles is configured to allow the user to move the lower leg support manually. The knee therapy device also includes a stay, where the stay is configured to prevent overextension of the user's knee joint and a stop, where the stop is adjustable and stops flexion of the user's knee joint. The knee therapy device further includes a resistance device, where the resistance device is configured to allow the user to determine the amount of force required to move the lower leg support and a counter, where the counter keeps track of a number of repetitions of movement of the user's knee joint through a prescribed range of motion.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1A:
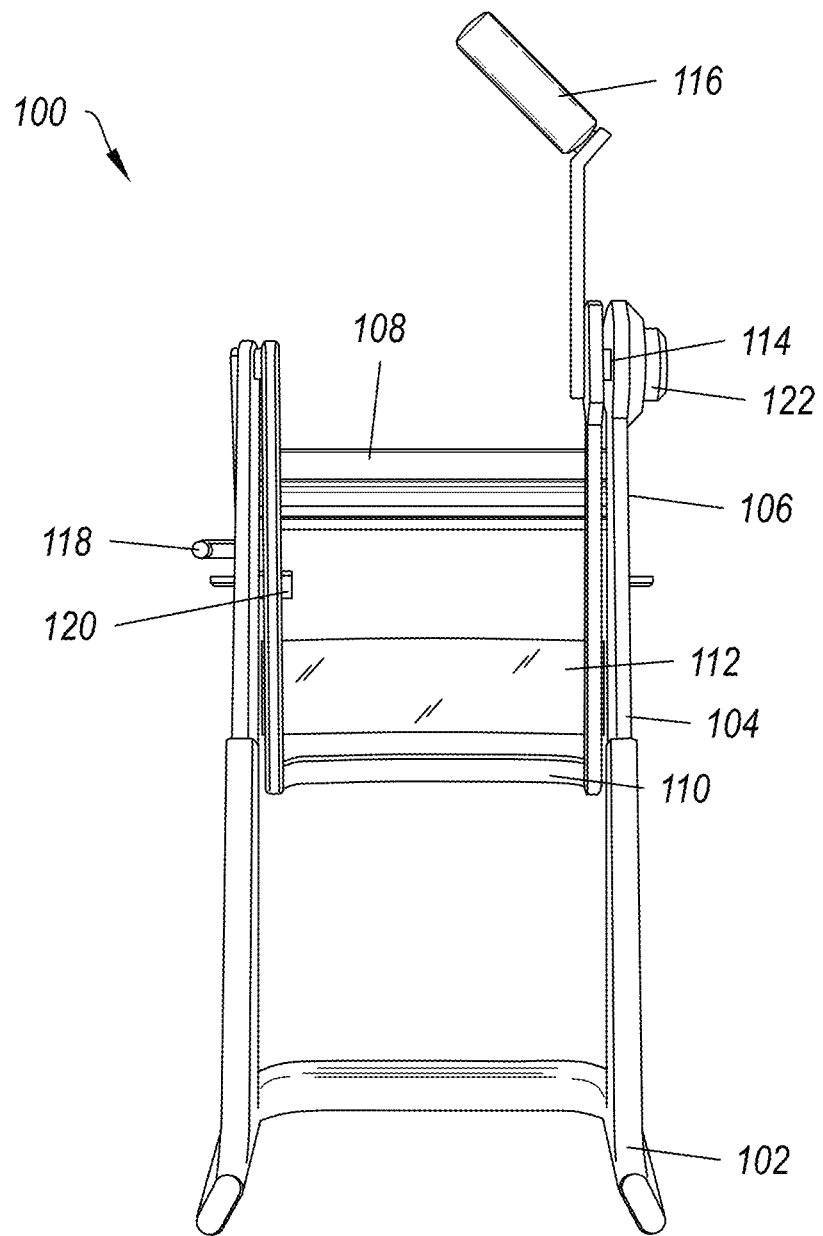
FIG. 1A illustrates a rear view of the knee therapy device.
Figure 1B:
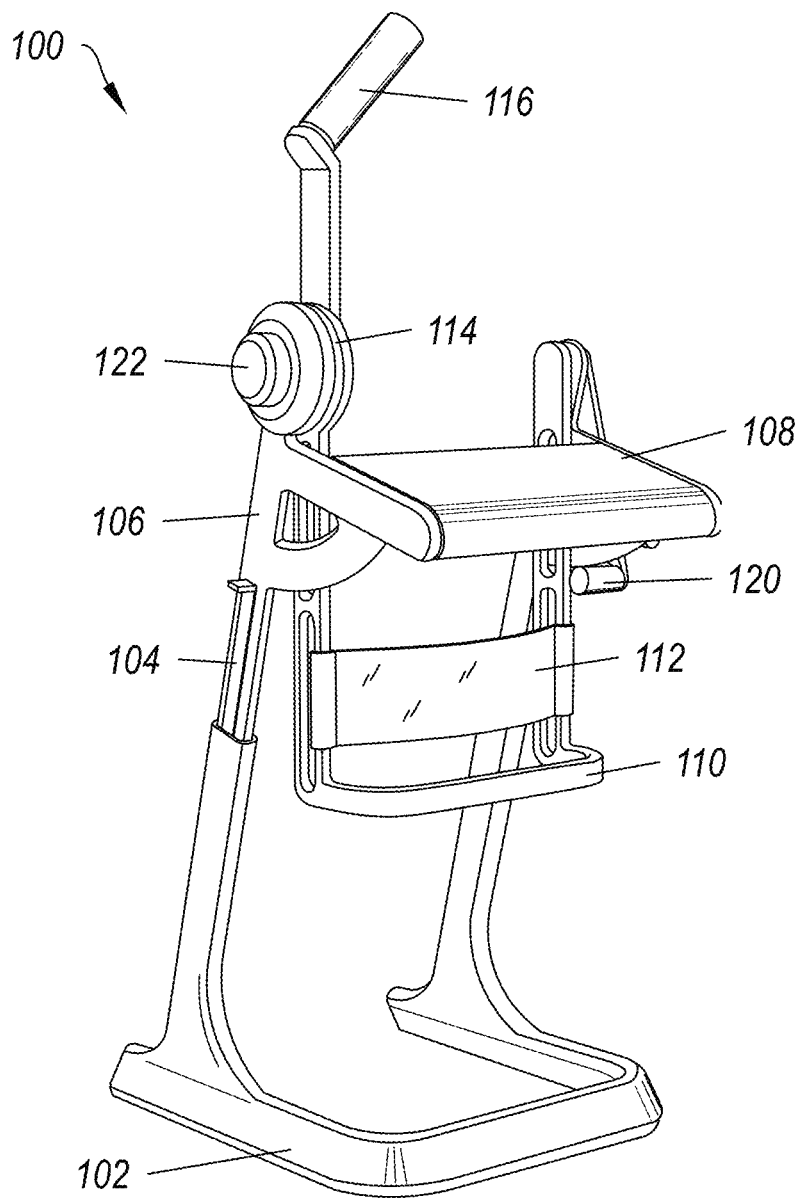
FIG. 1B illustrates a front right view of the knee therapy device.
Figure 1C:
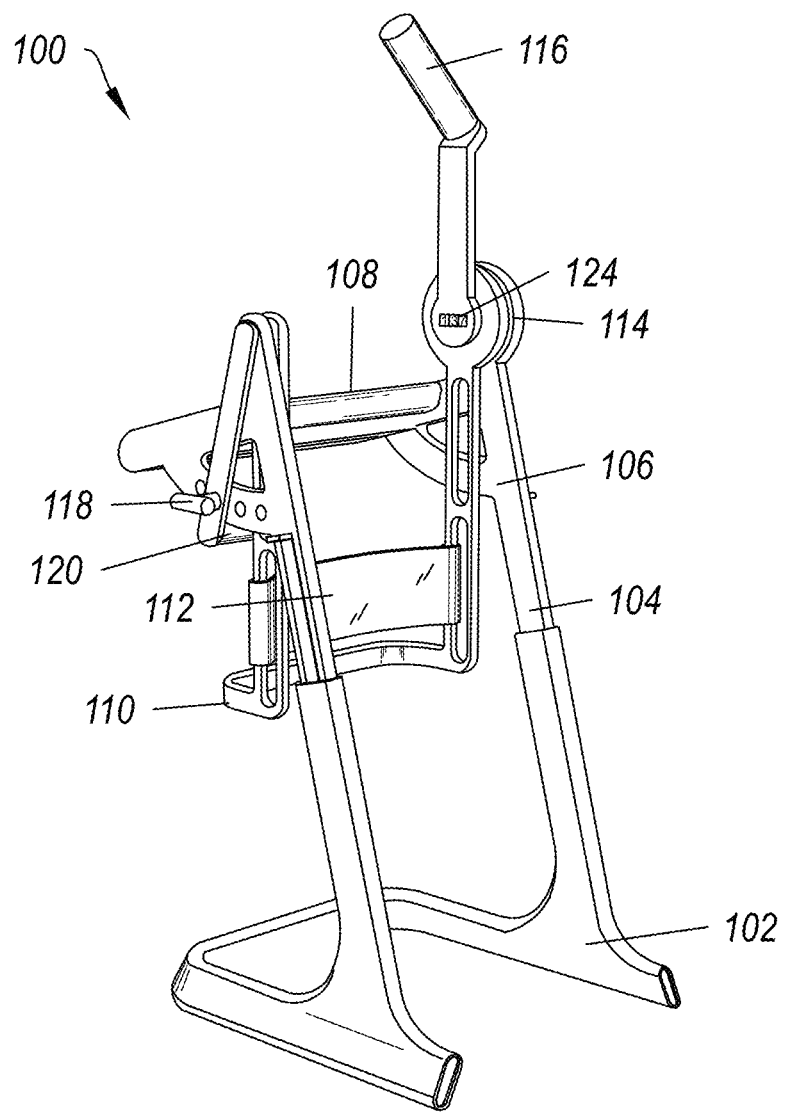
FIG. 1C illustrates a left rear view of the knee therapy device.
Figure 1D:
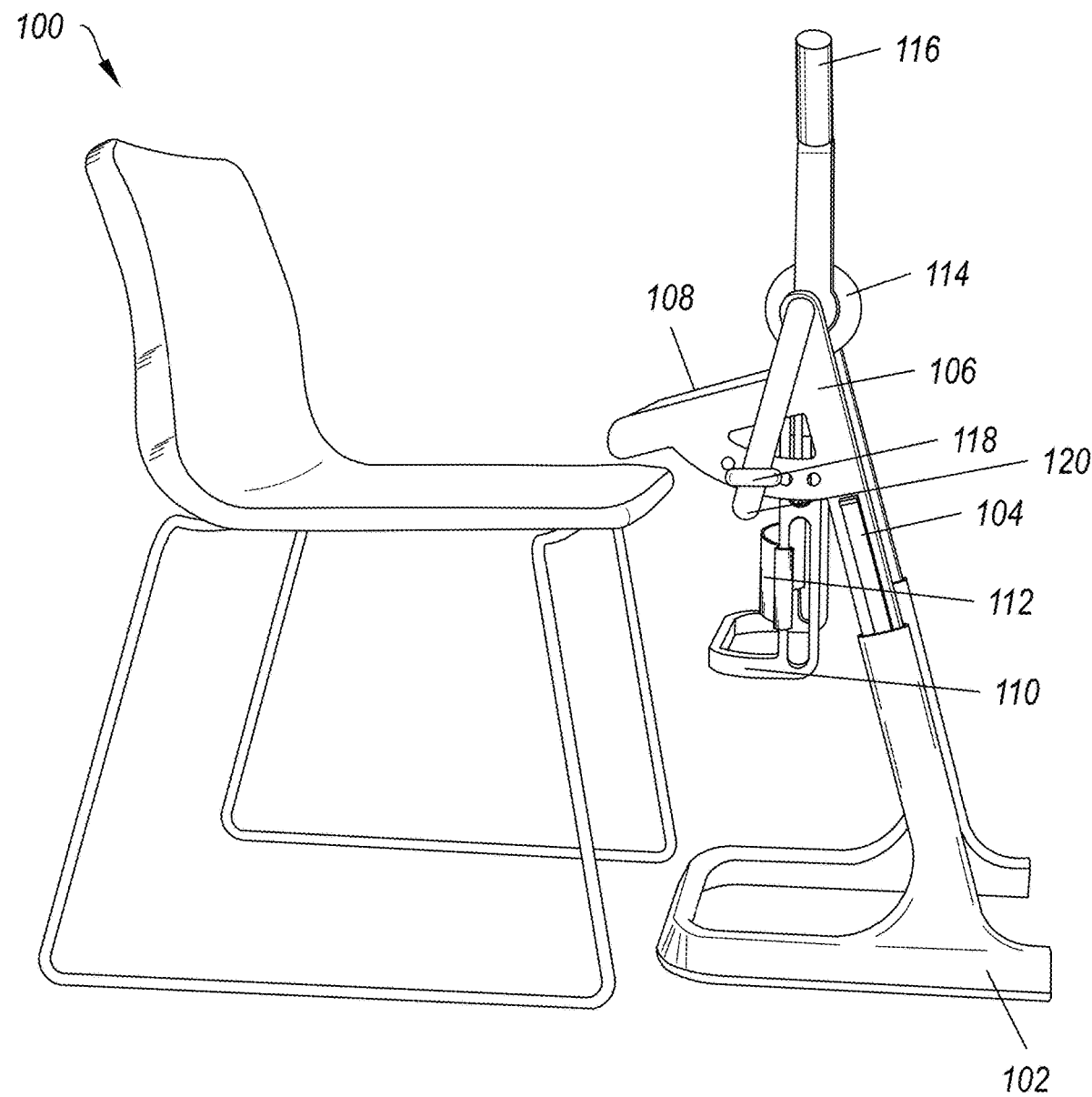
FIG. 1D illustrates a left view of the knee therapy device with a chair for perspective on where a user would sit relative to the knee therapy device.
Figure 1E:
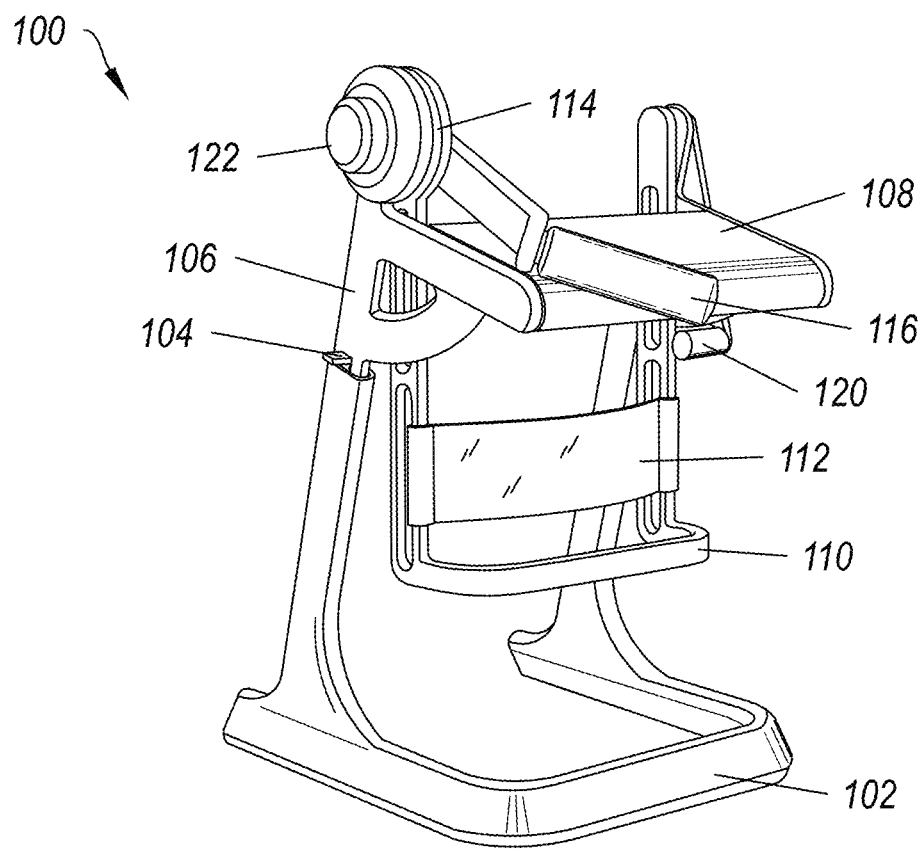
FIG. 1E illustrates a front right view of the knee therapy device folded.

FIGS. 1A-1E (collectively "FIG. 1") illustrate an example of a knee therapy device 100. FIG. 1A illustrates a rear view of the knee therapy device 100; FIG. 1B illustrates a front right view of the knee therapy device 100; FIG. 1C illustrates a left rear view of the knee therapy device 100; FIG. 1D illustrates a left view of the knee therapy device 100 with a chair for perspective on where a user would sit relative to the knee therapy device 100; and FIG. 1E illustrates a front right view of the knee therapy device 100 folded. The knee therapy device 100 assists a patient with physical therapy. For example, after a knee injury or knee surgery a patient often needs to move a leg at the knee joint to preserve or increase range of motion. Traditionally, this is done by having a physical therapist or other person move the leg for the patient. This forces movement of the joint without the joint having to support weight or otherwise be involved in ways that could lead to permanent injury. The drawback of this method is that the physical therapist must look for cues as to pain tolerance, mobility, strength, etc. Instead, the knee therapy device 100 allows the patient to control the movement of his/her leg and the resistance applied to the joint. This allows the patient to control more parameters of the physical therapy, leading to decreased recovery times.

FIG. 1 shows that the knee therapy device 100 can include a base 102. The base 102 supports the weight of the knee therapy device 100. Having a sufficient base 102 is critical for the operation of the knee therapy device 100. Because the patient may not be able to support any weight on his/her knee joint the base 102 must be sufficient to hold the user's leg in a stable position. Patients will naturally try to catch their weight with their leg if they feel unstable. That can lead to increased joint damage. Therefore, it is important that the base 102 be stable and secure.

FIG. 1 also shows that the knee therapy device 100 can include one or more legs 104. The one or more legs 104 connect the base 102 to the rest of the knee therapy device 100. That is, the one or more legs 104 support the rest of the knee therapy device 100 via the base 102. The height of the one or more legs 104 can be adjustable to allow the knee therapy device to be adjusted based on user. Height adjustment of the legs 104 can be critical to allow the height of the knee therapy device 100 to be adjusted to accommodate users. I.e., if the height of the one or more legs 104 is too large or too small, then it can cause strain on the user's knee or other joints.

In addition, by allowing the length of the legs 104 to be adjusted, the knee therapy device 100 can be made compact to facilitate transportation. This can be critical because it allows the knee therapy device 100 to be transported to the user. If the user can use the knee therapy device 100 at his/her home then they are much more likely to actually use the device, which will decrease recovery time and lead to greater joint flexibility long-term. Thus, anything that makes the knee therapy device 100 more portable is critical to its success in therapy.

FIG. 1 further shows that the knee therapy device 100 can include a frame 106. The frame 106 supports the other portions of the knee therapy device 100 and in turn is supported by the one or more legs 106. That is, the frame 106 provides support for the other portions of the knee therapy device 100 and for the user's leg, as described below. The frame 106 is attached to the one or more legs 104. One of skill in the art will appreciate that the frame 106, one or more legs 104, and/or base 102 can be a single piece or can be multiple elements attached to one another.

FIG. 1 additionally shows that the knee therapy device 100 includes a thigh pad 108. The thigh pad 108 is configured to support the upper leg of the user during use. That is, the user places his/her thigh on the thigh pad 108. The thigh pad 108 provides support to the upper leg to prevent its movement and to give stability to the knee joint. Stability is critical to prevent further damage to the user's knee, thus the thigh pad 108 does not move relative to the frame 106.

As used in the specification and the claims, the phrase "configured to" denotes an actual state of configuration that fundamentally ties recited elements to the physical characteristics of the recited structure. That is, the phrase "configured to" denotes that the element is structurally capable of performing the cited element but need not necessarily be doing so at any given time. Thus, the phrase "configured to" reaches well beyond merely describing functional language or intended use since the phrase actively recites an actual state of configuration.

The thigh pad 108 includes a comfortable resting place for the thigh of the user. For example, the thigh pad can include padding and a cover. The cover can include materials that make the leg of the user comfortable. For example, the padding can include foam and the covering can include leather or cloth.

FIG. 1 moreover shows that the knee therapy device 100 can include a lower leg support 110. The lower leg support 110 is configured to support the lower leg of the user. The lower leg support 110 can be sized and placed to support the lower leg at any point from the calf to the ankle of the user. The lower leg support 110 moves relative to the frame 106. This allows the user to move his/her lower leg relative to his/her thigh. However, side to side movement of the lower leg support 110 is restricted to prevent torque on the knee joint of the user. I.e., there is a hinge point around which the lower leg support 110 can move which allows the knee joint of the user to move back and forth.

FIG. 1 also shows that the knee therapy device 100 can include a strap 112. The strap 112 is configured to secure the user's lower leg to the lower leg support 110. That is, the strap goes across the shin of the user to keep his/her lower leg pressed against the lower leg support 110. This allows the user to go through both extension and flexion when moving his/her knee joint. I.e., when the user is extending the knee joint, the user's lower leg presses against the strap 112, and during flexion it presses against the lower leg support 110.

FIG. 1 further shows that the knee therapy device 100 can include a hinge 114. The hinge 114 connects the lower leg support 110 to the frame 106. This allows movement of the lower leg support 110 in a single plane. I.e., the lower leg support 110 can move in an arc around the hinge 114. If the hinge is placed at or near the rotation point (i.e., within 2-3 inches of the axis) of the user's knee then the movement of the lower leg support 110 conforms to the bending of the knee joint of the user. This location of the rotation point can be critical for multiple reasons. For example, some of the benefits of placement of the hinge 114 can include:

1. Increases synovial fluid in the joint which in turn delivers bio nutrients to the joint and the surrounding tissues.
2. Controlled, rhythmical motion decreases pain by activating the "gait mechanism" neurologically inhibiting the pain pathways to the brain.
3. Prevents and remodels scar tissue, adhesions and fibrin formation in and around the joint.
4. The above prevents the need for post-surgical manipulation of the scar tissue.
5. Increases active, active assisted, and passive range of motion.

6. Facilitates muscle memory and motor patterns for regaining "normal knee" movements (neuromuscular facilitation).
7. Decreases muscle guarding (where a user contracts his/her muscle to prevent movement of the joint, which places tension on the joint).
8. Slow, controlled, rhythmical motion can decrease swelling and assist with lymphatic drainage.
9. Depending on pace (speed), force (thrust) and range of motion (distance) joint manipulation is achieved. (grades I, II, III, and IV)
10. Increases tissue temperatures and elasticity thus improving muscle flexibility and preventing soft tissue contracture and adhesive capsulitis.
11. Repetitive successful treatments cause psychological confidence in the patient.
12. Increases neuromuscular facilitation (increased coordination of muscles in moving the joint).

FIG. 1 additionally shows that the knee therapy device 100 can include a handle 116. The handle 116 is configured to allow the user to move the lower leg support 110 about the hinge 114 manually (that is, without the use of the user's leg muscles). I.e., the user can move the lower leg support 110 by applying pressure via bending/extending his/her knee, by moving the handle 116, or a combination of the two. This allows the user to user extend his/her range of motion in bending the knee joint. I.e., the user may be only to bend the knee joint a certain amount naturally (e.g., from straight to 45 degrees) but the handle 116 allows him/her to bend the knee joint further (e.g., all the way to a 90-degree bend) which stretches the user's tendons and increases the user's range of motion. This combination of active and passive movement to increase range of motion is known as active-assisted range of motion.

Additionally or alternatively, the handle 116 can allow the user to flex the knee joint without extending the knee joint or vice versa. E.g., the user can flex his/her knee joint using his/her muscles and then extend the knee joint using the handle 116. Thus, the user can perform as much activity as possible. This means that the user can work the joint passively (handle 116 only and no leg muscles engagement), actively assisted (handle 116 and leg muscles) and active (leg muscles only, without assistance from the handle 116). This means that virtually any patient can use the knee therapy device 100.

The handle 116 can fold down against the thigh pad 108. That allows the device to fold into a smaller profile. This is critical, because users are far more likely to use a device that they can use at home, than a device that can only be accessed at a remote location, such as a doctor's office. When completely folded the entire knee therapy device 100 can be placed in a gym bag or backpack of approximate size 24 inches long by 22 inches wide by 30 inches tall. This compactness and lightness creates portability that other devices lack. This, in turn, leads to other benefits such as when the patient can perform the activity themselves without anyone else around their fear and apprehension regarding potential pain and injury decreases. As used in the specification and the claims, the term approximately shall mean that the value is within 10% of the stated value, unless otherwise specified.

FIG. 1 also shows that the knee therapy device 100 can include a stop 118. The stop 118 allows the user to set a maximum range of motion. I.e., the stop 118 prevents movement of the lower leg support 110 about the hinge 114 at a desired point. This prevents too much flexion of the knee joint. The user can adjust the stop 118 based on physician's orders or to maximize physiological healing how much he/she can bend his/her knee. I.e., the stop 118 is adjustable to allow a different range of motion for the user. As shown, the stop 118 is push button so the user pushes in the selector (or pulls out the selector, depending on one's perspective) and then the stop automatically clicks into place in predetermined spots along the frame 106. Depending on the patient's natural range of motion, the stop 118 can allow the user to flex the knee joint up to 130 degrees. However, the range of motion can be limited to some lower amount of flexion, based on the needs of the user.

FIG. 1 further shows that the knee therapy device 100 can include a stay 120. The stay 120 prevents over extension of the user's knee joint. In general, the user will not overextend his/her knee normally, but if the stay 120 is not in place then overextension can occur by use of the handle 116. I.e., the stay 120 prevents force on the handle 116 from overextending the knee joint. The stay 120 can allow extension of the user's knee up to −10 degrees. While this would be hyperextension in some user's it is quite common for women's knees to extend this far; thus, to obtain a full range of motion the stay 120 allows for this extended range of motion. However, the range of motion can be limited to some lower amount of extension, based on the needs of the user.

FIG. 1 additionally shows that the knee therapy device 100 can include a resistance device 122. The resistance device 122 is configured to allow the user to determine the amount of force required to move the lower leg support 110. I.e., the higher the resistance setting on the resistance device 122, the more difficult it is to move the lower leg support 110. This allows the user to increase muscle mass around the knee joint, providing greater muscular support to the joint. I.e., the resistance device 122 can be critical to strengthen the muscles around the knee joint which allows the patient to recover faster and to decrease chances of hurting the knee joint during physical therapy.

The resistance device 100 can include any desired mechanism that allows the user to change the resistance. For example, the resistance device 122 as shown in FIG. 1 is a resistance dial. The user turns the dial one direction to increase the resistance and the opposite direction to decrease the resistance. However, one of skill in the art will appreciate that other resistance devices 122 such as elastic bands and/or weights can be used in place of the resistance dial.

FIG. 1 moreover shows that the knee therapy device 100 can include a counter 124. The counter 124 allows the user to keep track of how many repetitions the user has undergone. That is, each time the user moves the joint through the prescribed range of motion, the counter goes up by one. This can also be accessed by a caregiver, such as a physical therapist, nurse, doctor, etc.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A knee therapy device, the knee therapy device comprising:
   a base;
   one or more legs attached to the base;
   a frame, the frame attached to the one or more legs;
   a thigh pad attached to the frame, wherein the thigh pad is configured to support the thigh of a user;

a lower leg support, wherein the lower leg support:
   is attached to the frame; and
   is configured to support the lower leg of the user;
a hinge, wherein the hinge allows the lower leg support to move relative to the frame;
a strap, wherein the strap is configured to secure the user's lower leg relative to the lower leg support;
a handle, wherein the handle is configured to allow the user to move the lower leg support manually;
a stay, wherein the stay is configured to prevent overextension of the user's knee joint;
a stop, wherein the stop:
   is adjustable; and
   stops flexion of the user's knee joint;
a resistance device, wherein the resistance device is configured to allow the user to determine the amount of force required to move the lower leg support; and
a counter, wherein the counter keeps track of a number of repetitions of movement of the user's knee joint through a prescribed range of motion.

2. The knee therapy device of claim 1, wherein a thigh pad includes padding.

3. The knee therapy device of claim 2, wherein the padding includes foam.

4. The knee therapy device of claim 1, wherein the thigh pad includes a covering.

5. The knee therapy device of claim 4, wherein the covering includes cloth.

6. The knee therapy device of claim 4, wherein the covering includes leather.

7. The knee therapy device of claim 1, wherein a length of the one or more legs is adjustable.

8. The knee therapy device of claim 1, wherein the strap is configured to be placed on the shin of the user.

9. The knee therapy device of claim 1, wherein the hinge is located at or near the rotation point of the user's knee.

10. The knee therapy device of claim 1, wherein the range of motion of the lower leg support is adjustable.

11. The knee therapy device of claim 1, wherein the handle is configured to fold against the thigh pad.

12. The knee therapy device of claim 1, wherein the resistance device includes a resistance dial.

13. The knee therapy device of claim 1, wherein the stop includes a push button selector, wherein the push button selector allows the user to adjust the position of the stop.

14. The knee therapy device of claim 1, wherein:
   the stop allows extension of the user's knee up to approximately negative 10 degrees; and
   the stay allows flexion of the user's knee up to approximately 130 degrees.

* * * * *